US012773146B2

(12) United States Patent
Patel et al.

(10) Patent No.: US 12,773,146 B2
(45) Date of Patent: Oct. 27, 2026

(54) AUTOMATED URINARY OUTPUT MEASURING SYSTEM

(71) Applicant: C. R. Bard, Inc., Franklin Lakes, NJ (US)

(72) Inventors: Hersh Ramesh Patel, Atlanta, GA (US); Varad Chavan, Kolhapur (IN); Thomas Michael Meese, Louisville, CO (US); Dennis Joseph, Milton, GA (US); Rachit Bhasin, Chandigarh (IN)

(73) Assignee: C. R. Bard, Inc., Franklin Lakes, NJ (US)

( * ) Notice: Subject to any disclaimer, the term of this patent is extended or adjusted under 35 U.S.C. 154(b) by 759 days.

(21) Appl. No.: 17/883,507

(22) Filed: Aug. 8, 2022

(65) Prior Publication Data

US 2023/0060232 A1 Mar. 2, 2023

Related U.S. Application Data

(60) Provisional application No. 63/237,085, filed on Aug. 25, 2021.

(51) Int. Cl.
*A61B 5/20* (2006.01)
*A61B 5/00* (2006.01)
(Continued)

(52) U.S. Cl.
CPC .............. *A61B 5/208* (2013.01); *A61B 5/743* (2013.01); *A61B 5/7475* (2013.01); *A61B 50/20* (2016.02);
(Continued)

(58) Field of Classification Search
CPC . A61B 2562/0271; A61B 5/002; A61B 5/208; A61B 5/743; A61B 5/7475;
(Continued)

(56) References Cited

U.S. PATENT DOCUMENTS

| | | | |
|---|---|---|---|
| 3,661,143 | A | 5/1972 | Henkin |
| 3,781,920 | A | 1/1974 | Browne et al. |

(Continued)

FOREIGN PATENT DOCUMENTS

| | | | |
|---|---|---|---|
| CA | 2882654 | A1 | 10/2007 |
| CN | 2445749 | Y | 9/2001 |

(Continued)

OTHER PUBLICATIONS

U.S. Appl. No. 15/748,107, filed Jan. 26, 2018 Notice of Allowance dated Dec. 12, 2022.

(Continued)

*Primary Examiner* — Benjamin S Melhus
(74) *Attorney, Agent, or Firm* — Rutan & Tucker LLP

(57) ABSTRACT

Disclosed herein is an automated urinary output monitoring system including an automated urinary output monitoring device. The automated urinary output monitoring device includes a load cell assembly, a mounting system having a buffering region configured to reduce vibrations through the automated urinary output monitoring device and allow axial rotation of the automated urinary output monitoring device around a lateral axis, a mounting region configured to couple the automated urinary output monitoring device to a surface, a fluid collection bag attachment, and a console in communication with the load cell assembly.

16 Claims, 7 Drawing Sheets

(51) Int. Cl.
*A61B 50/20* (2016.01)
*G16H 10/60* (2018.01)

(52) U.S. Cl.
CPC ...... *G16H 10/60* (2018.01); *A61B 2562/0271* (2013.01)

(58) Field of Classification Search
CPC ..... A61B 50/20; A61B 10/007; A61B 5/0004; A61B 5/6891; A61B 5/7225; A61B 5/742; A61B 2560/0475; A61B 2562/0233; A61B 5/00; A61B 5/7425; A61B 5/7435; A61B 5/7445; A61B 2505/03; A61B 2505/07; A61B 2560/0443; A61B 2562/0214; A61B 2562/0219; A61B 2562/0261; A61B 5/7207; A61B 5/7278; G16H 10/60; G16H 15/00; G16H 40/63; A61M 25/0017; A61M 1/70; A61M 1/83; A61M 2202/0496; A61M 2205/123; A61M 2205/3306; A61M 2205/3334; A61M 2205/3389; A61M 2205/505; A61M 25/0097; A61M 39/08; A61M 39/28; A61M 39/284
See application file for complete search history.

(56) References Cited

U.S. PATENT DOCUMENTS 3,851,650 A 12/1974 Darling
3,919,455 A 11/1975 Sigdell et al.
4,276,889 A 7/1981 Kuntz et al.
4,286,590 A 9/1981 Murase
4,291,692 A 9/1981 Bowman et al.
4,296,749 A 10/1981 Pontifex
4,305,405 A 12/1981 Meisch
4,312,352 A 1/1982 Meisch et al.
4,343,316 A 8/1982 Jespersen
4,443,219 A 4/1984 Meisch et al.
4,448,207 A 5/1984 Parrish
4,509,366 A 4/1985 Matsushita et al.
4,532,936 A 8/1985 LeVeen et al.
4,658,834 A 4/1987 Blankenship et al.
4,712,567 A 12/1987 Gille et al.
4,723,950 A 2/1988 Lee
4,763,739 A 8/1988 Kasinoff
4,834,706 A 5/1989 Beck et al.
4,850,375 A 7/1989 Rosenberg
4,889,532 A 12/1989 Metz et al.
5,002,541 A 3/1991 Conkling et al.
5,146,637 A 9/1992 Bressler et al.
5,188,327 A 2/1993 White
5,409,014 A 4/1995 Napoli et al.
5,586,085 A 12/1996 Lichte
5,725,515 A 3/1998 Propp
5,733,319 A 3/1998 Neilson et al.
5,738,656 A 4/1998 Wagner
5,747,824 A 5/1998 Jung et al.
5,769,087 A 6/1998 Westphal et al.
5,807,278 A 9/1998 McRae
5,823,972 A 10/1998 McRae
5,891,051 A 4/1999 Han et al.
5,911,786 A 6/1999 Nielsen et al.
6,129,684 A 10/2000 Sippel et al.
6,132,407 A 10/2000 Genese et al.
6,250,152 B1 6/2001 Klein et al.
6,256,532 B1 7/2001 Cha
6,261,254 B1 7/2001 Baron et al.
6,434,418 B1 8/2002 Neal et al.
6,454,372 B1 9/2002 Yang
6,579,247 B1 6/2003 Abramovitch et al.
6,592,612 B1 7/2003 Samson et al.
6,709,420 B1 3/2004 Lincoln et al.
6,716,200 B2 4/2004 Bracken et al.
7,011,634 B2 3/2006 Paasch et al.
7,161,484 B2 1/2007 Tsoukalis
7,211,037 B2 5/2007 Briggs et al.
7,437,945 B1 10/2008 Feller
7,442,754 B2 10/2008 Tepper et al.
7,722,584 B2 5/2010 Tanaka et al.
7,739,907 B2 6/2010 Boiarski
7,871,385 B2 1/2011 Levinson
7,931,630 B2 4/2011 Nishtala et al.
7,976,533 B2 7/2011 Larsson
7,998,126 B1 8/2011 Fernandez
8,295,933 B2 10/2012 Gerber et al.
8,328,733 B2 12/2012 Forte et al.
8,328,734 B2 12/2012 Salvadori et al.
8,337,476 B2 12/2012 Greenwald et al.
8,374,688 B2 2/2013 Libbus et al.
8,403,884 B2 3/2013 Nishtala
8,471,231 B2 6/2013 Paz
8,663,128 B2 3/2014 Paz et al.
8,773,259 B2 7/2014 Judy et al.
8,790,277 B2 7/2014 Elliott et al.
8,790,320 B2 7/2014 Christensen
8,790,577 B2 7/2014 Mizumoto et al.
8,813,551 B2 8/2014 Boiarski
8,827,924 B2 9/2014 Paz et al.
8,832,558 B2 9/2014 Cardarelli et al.
8,900,196 B2 12/2014 Andino
9,045,887 B2 6/2015 O'Malley
9,050,046 B2 6/2015 Elliott et al.
9,074,920 B2 7/2015 Mendels et al.
9,216,242 B2 12/2015 Nishtala et al.
9,480,821 B2 11/2016 Ciccone et al.
9,592,034 B2 3/2017 Hall et al.
9,642,987 B2 5/2017 Bierman et al.
9,731,097 B2 8/2017 Andino et al.
9,895,095 B2 2/2018 Chen
9,928,341 B2 3/2018 Angelides
9,962,516 B2 5/2018 Lampotang et al.
10,071,202 B2 9/2018 Handler
10,182,747 B2 1/2019 Charlez et al.
10,245,008 B2 4/2019 Paige
10,301,807 B1 5/2019 Kolesar
10,362,981 B2 7/2019 Paz et al.
10,383,606 B1 8/2019 McCord et al.
10,448,875 B2 10/2019 Holt et al.
10,722,679 B2 * 7/2020 Lampotang ....... A61M 25/0017
10,799,386 B1 10/2020 Harrison, Sr.
10,881,320 B2 1/2021 Duval et al.
10,881,778 B2 1/2021 Scarpaci et al.
11,291,577 B2 4/2022 Seres et al.
11,473,958 B2 10/2022 Holt et al.
11,540,760 B1 1/2023 Guillemette
11,654,042 B2 * 5/2023 Hughett, Sr. ......... A61F 5/4404 600/581
11,703,365 B2 7/2023 Tourchak et al.
12,083,261 B2 9/2024 Justice et al.
12,109,353 B2 10/2024 Cheng et al.
12,364,423 B2 7/2025 Cheng et al.
12,408,853 B2 9/2025 Kriscovich et al.
2001/0056226 A1 12/2001 Zodnik et al.
2002/0013518 A1 1/2002 West et al.
2002/0016719 A1 2/2002 Nemeth et al.
2002/0161314 A1 10/2002 Sarajarvi
2002/0193760 A1 12/2002 Thompson
2003/0000303 A1 1/2003 Livingston et al.
2003/0140697 A1 7/2003 Van Ee
2003/0163183 A1 8/2003 Carson
2003/0163287 A1 8/2003 Vock et al.
2004/0267086 A1 12/2004 Anstadt et al.
2005/0020958 A1 1/2005 Paolini et al.
2005/0065583 A1 3/2005 Voorhees et al.
2005/0172712 A1 8/2005 Nyce
2005/0247121 A1 11/2005 Pelster
2006/0065713 A1 3/2006 Kingery
2006/0100743 A1 5/2006 Townsend et al.
2006/0253091 A1 11/2006 Vernon
2007/0010797 A1 1/2007 Nishtala et al.
2007/0078444 A1 4/2007 Larsson

(56) References Cited

U.S. PATENT DOCUMENTS

| | | | |
|---|---|---|---|
| 2007/0106177 A1 | 5/2007 | Hama | |
| 2007/0145137 A1 | 6/2007 | Mrowiec | |
| 2007/0225668 A1 | 9/2007 | Otto | |
| 2007/0252714 A1 | 11/2007 | Rondoni et al. | |
| 2008/0027409 A1 | 1/2008 | Rudko et al. | |
| 2008/0217391 A1 | 9/2008 | Roof et al. | |
| 2008/0312550 A1 | 12/2008 | Nishtala et al. | |
| 2008/0312556 A1 | 12/2008 | Dijkman | |
| 2009/0056020 A1 | 3/2009 | Caminade et al. | |
| 2009/0099629 A1 | 4/2009 | Carson et al. | |
| 2009/0157430 A1 | 6/2009 | Rule et al. | |
| 2009/0171169 A1 | 7/2009 | Nagata | |
| 2009/0287170 A1 | 11/2009 | Otto | |
| 2009/0315684 A1 | 12/2009 | Sacco et al. | |
| 2010/0064426 A1 | 3/2010 | Chikara Imamura | |
| 2010/0094204 A1 | 4/2010 | Nishtala | |
| 2010/0122963 A1 | 5/2010 | Costa et al. | |
| 2010/0130949 A1 | 5/2010 | Garcia | |
| 2010/0137743 A1 | 6/2010 | Nishtala et al. | |
| 2010/0262047 A1 | 10/2010 | Genis | |
| 2011/0113540 A1 | 5/2011 | Plate et al. | |
| 2011/0120219 A1 | 5/2011 | Barlesi et al. | |
| 2011/0178425 A1 | 7/2011 | Nishtala et al. | |
| 2011/0224636 A1 | 9/2011 | Keisic | |
| 2011/0230824 A1 | 9/2011 | Salinas et al. | |
| 2011/0238042 A1 | 9/2011 | Davis et al. | |
| 2011/0251572 A1 | 10/2011 | Nishtala et al. | |
| 2011/0263952 A1 | 10/2011 | Bergman et al. | |
| 2012/0029408 A1 | 2/2012 | Beaudin | |
| 2012/0035496 A1 | 2/2012 | Denison et al. | |
| 2012/0059286 A1 | 3/2012 | Hastings et al. | |
| 2012/0078137 A1 | 3/2012 | Mendels et al. | |
| 2012/0078235 A1 | 3/2012 | Martin et al. | |
| 2012/0095304 A1 | 4/2012 | Biondi | |
| 2012/0108917 A1 | 5/2012 | Libbus et al. | |
| 2012/0109008 A1 | 5/2012 | Charlez et al. | |
| 2012/0118650 A1 | 5/2012 | Gill | |
| 2012/0123233 A1 | 5/2012 | Cohen | |
| 2012/0127103 A1 | 5/2012 | Qualey et al. | |
| 2012/0226196 A1 | 9/2012 | DiMino et al. | |
| 2012/0234434 A1 | 9/2012 | Woodruff et al. | |
| 2012/0302917 A1 | 11/2012 | Fitzgerald et al. | |
| 2012/0323144 A1 | 12/2012 | Coston et al. | |
| 2012/0323502 A1 | 12/2012 | Tanoura et al. | |
| 2013/0066166 A1 | 3/2013 | Bumett et al. | |
| 2013/0109927 A1 | 5/2013 | Menzel | |
| 2013/0109928 A1 | 5/2013 | Menzel | |
| 2013/0131610 A1 | 5/2013 | Dewaele et al. | |
| 2013/0218106 A1 | 8/2013 | Coston et al. | |
| 2013/0245498 A1 | 9/2013 | Delaney et al. | |
| 2013/0256486 A1 | 10/2013 | Taylor | |
| 2013/0267871 A1 | 10/2013 | Delaney et al. | |
| 2014/0039348 A1 | 2/2014 | Bullington et al. | |
| 2014/0155781 A1 | 6/2014 | Bullington et al. | |
| 2014/0155782 A1 | 6/2014 | Bullington et al. | |
| 2014/0159921 A1 | 6/2014 | Qualey et al. | |
| 2014/0166691 A1 | 6/2014 | Chen et al. | |
| 2014/0187666 A1 | 7/2014 | Aizenberg et al. | |
| 2014/0207085 A1 | 7/2014 | Brandt et al. | |
| 2014/0243635 A1 | 8/2014 | Arefieg | |
| 2014/0335490 A1 | 11/2014 | Baarman et al. | |
| 2015/0120321 A1 | 4/2015 | David et al. | |
| 2015/0233749 A1 | 8/2015 | Wang et al. | |
| 2015/0342576 A1 | 12/2015 | Hall et al. | |
| 2015/0343173 A1 | 12/2015 | Tobescu et al. | |
| 2015/0359522 A1 | 12/2015 | Recht et al. | |
| 2015/0362351 A1 | 12/2015 | Joshi et al. | |
| 2016/0051176 A1 | 2/2016 | Ramos et al. | |
| 2016/0051177 A1* | 2/2016 | Chen .................... | G01N 33/493<br>600/573 |
| 2016/0183819 A1 | 6/2016 | Burnett et al. | |
| 2016/0374874 A1 | 12/2016 | Trepanier et al. | |
| 2017/0035342 A1 | 2/2017 | Elia et al. | |
| 2017/0043089 A1 | 2/2017 | Handler | |
| 2017/0100068 A1 | 4/2017 | Kostov | |
| 2017/0113000 A1 | 4/2017 | Tobescu et al. | |
| 2017/0136209 A1 | 5/2017 | Burnett et al. | |
| 2017/0140103 A1 | 5/2017 | Angelides | |
| 2017/0196478 A1 | 7/2017 | Hunter | |
| 2017/0202698 A1 | 7/2017 | Zani et al. | |
| 2017/0241978 A1 | 8/2017 | Duval | |
| 2017/0249445 A1 | 8/2017 | Devries et al. | |
| 2017/0290540 A1 | 10/2017 | Franco | |
| 2017/0291012 A1 | 10/2017 | Iglesias | |
| 2017/0307423 A1 | 10/2017 | Pahwa et al. | |
| 2017/0322197 A1 | 11/2017 | Hall et al. | |
| 2018/0015251 A1 | 1/2018 | Lampotang et al. | |
| 2018/0110455 A1 | 4/2018 | Chang et al. | |
| 2018/0110456 A1 | 4/2018 | Cooper et al. | |
| 2018/0160961 A1 | 6/2018 | Gopinathan et al. | |
| 2018/0214122 A1 | 8/2018 | Ansell et al. | |
| 2018/0214297 A1 | 8/2018 | Hughett et al. | |
| 2018/0245967 A1 | 8/2018 | Parker et al. | |
| 2018/0280236 A1 | 10/2018 | Ludin et al. | |
| 2018/0306661 A1 | 10/2018 | Stacey | |
| 2018/0317891 A1 | 11/2018 | Kim | |
| 2018/0344234 A1 | 12/2018 | McKinney et al. | |
| 2018/0344295 A1 | 12/2018 | Leibman | |
| 2019/0006047 A1 | 1/2019 | Gorek et al. | |
| 2019/0017535 A1 | 1/2019 | Ormsbee et al. | |
| 2019/0046102 A1 | 2/2019 | Kushnir et al. | |
| 2019/0069829 A1 | 3/2019 | Bulut | |
| 2019/0069830 A1 | 3/2019 | Holt et al. | |
| 2019/0126006 A1 | 5/2019 | Rehm et al. | |
| 2019/0150821 A1 | 5/2019 | Waters et al. | |
| 2019/0167144 A1 | 6/2019 | Jung et al. | |
| 2019/0201596 A1 | 7/2019 | Luxon et al. | |
| 2019/0218826 A1 | 7/2019 | Allen et al. | |
| 2019/0223844 A1 | 7/2019 | Aboagye et al. | |
| 2019/0231244 A1 | 8/2019 | Swan et al. | |
| 2019/0247236 A1 | 8/2019 | Sides et al. | |
| 2019/0254582 A1 | 8/2019 | Wei et al. | |
| 2019/0298317 A1 | 10/2019 | Colgan et al. | |
| 2019/0321588 A1 | 10/2019 | Burnett et al. | |
| 2019/0328945 A1 | 10/2019 | Analytis et al. | |
| 2019/0343445 A1 | 11/2019 | Burnett et al. | |
| 2019/0358387 A1 | 11/2019 | Elbadry et al. | |
| 2019/0365308 A1 | 12/2019 | Laing et al. | |
| 2019/0381223 A1 | 12/2019 | Culbert et al. | |
| 2020/0022637 A1 | 1/2020 | Kurzrock et al. | |
| 2020/0064172 A1 | 2/2020 | Tabaczewski et al. | |
| 2020/0085378 A1 | 3/2020 | Burnett et al. | |
| 2020/0121300 A1 | 4/2020 | Moore | |
| 2020/0187863 A1 | 6/2020 | Tu et al. | |
| 2020/0268302 A1 | 8/2020 | Oh | |
| 2020/0268303 A1 | 8/2020 | Oliva | |
| 2020/0289749 A1 | 9/2020 | Odashima et al. | |
| 2020/0405524 A1 | 12/2020 | Gill | |
| 2021/0000361 A1 | 1/2021 | Lark et al. | |
| 2021/0054610 A1 | 2/2021 | Hall et al. | |
| 2021/0077007 A1 | 3/2021 | Jouret et al. | |
| 2021/0098124 A1 | 4/2021 | Crook et al. | |
| 2021/0100533 A1 | 4/2021 | Seres et al. | |
| 2021/0113130 A1 | 4/2021 | Tran | |
| 2021/0202084 A1 | 7/2021 | Cronin et al. | |
| 2021/0298653 A1 | 9/2021 | Woodard et al. | |
| 2021/0299353 A1 | 9/2021 | Mannu et al. | |
| 2021/0361211 A1 | 11/2021 | Teramoto et al. | |
| 2022/0018692 A1 | 1/2022 | Tourchak et al. | |
| 2022/0026001 A1 | 1/2022 | Cheng et al. | |
| 2022/0026261 A1 | 1/2022 | Funnell et al. | |
| 2022/0079487 A1 | 3/2022 | Horiguchi et al. | |
| 2022/0192564 A1 | 6/2022 | Kriscovich et al. | |
| 2022/0192565 A1 | 6/2022 | Cheng et al. | |
| 2022/0192566 A1 | 6/2022 | Cheng et al. | |
| 2022/0193375 A1 | 6/2022 | Rehm et al. | |
| 2022/0233120 A1 | 7/2022 | Beuret et al. | |
| 2022/0296140 A1 | 9/2022 | Nguyen et al. | |
| 2022/0296406 A1 | 9/2022 | Keelen | |
| 2022/0330867 A1 | 10/2022 | Conley et al. | |
| 2022/0386917 A1 | 12/2022 | Mann et al. | |
| 2023/0000259 A1 | 1/2023 | Taylor | |
| 2023/0019703 A1 | 1/2023 | Behzad et al. | |
| 2023/0022547 A1 | 1/2023 | Cho et al. | |

(56) References Cited

U.S. PATENT DOCUMENTS

| | | | |
|---|---|---|---|
| 2023/0025333 | A1 | 1/2023 | Patel et al. |
| 2023/0028966 | A1 | 1/2023 | Franano |
| 2023/0035669 | A1 | 2/2023 | Raja et al. |
| 2023/0040915 | A1 | 2/2023 | Compton et al. |
| 2023/0058553 | A1 | 2/2023 | Fallows et al. |
| 2023/0084476 | A1 | 3/2023 | Robichaud et al. |
| 2023/0089041 | A1 | 3/2023 | Handler |
| 2024/0042120 | A1 | 2/2024 | Cheng et al. |
| 2024/0081708 | A1 | 3/2024 | Kelly et al. |
| 2024/0108268 | A1 | 4/2024 | Woodard et al. |
| 2024/0252783 | A1 | 8/2024 | Waitkus et al. |
| 2024/0347162 | A1 | 10/2024 | Meese et al. |
| 2024/0360938 | A1 | 10/2024 | Cheng et al. |
| 2024/0424186 | A1 | 12/2024 | Justice et al. |
| 2025/0090066 | A1 | 3/2025 | Tourchak |
| 2025/0120636 | A1 | 4/2025 | Compton et al. |
| 2025/0205456 | A1 | 6/2025 | Rehm et al. |
| 2025/0339073 | A1 | 11/2025 | Cheng et al. |
| 2026/0000330 | A1 | 1/2026 | Kriscovich et al. |
| 2026/0033762 | A1 | 2/2026 | Fallows et al. |
| 2026/0183468 | A1 | 7/2026 | Cheng et al. |

FOREIGN PATENT DOCUMENTS

| | | | |
|---|---|---|---|
| CN | 200951235 | Y | 9/2007 |
| CN | 201492414 | U | 6/2010 |
| CN | 102647939 | A | 8/2012 |
| CN | 103054559 | B | 5/2015 |
| CN | 104921738 | A | 9/2015 |
| CN | 205306875 | U | 6/2016 |
| CN | 107952140 | A | 4/2018 |
| CN | 109498013 | A | 3/2019 |
| CN | 110859636 | A | 3/2020 |
| CN | 112426156 | A | 3/2021 |
| EP | 0342028 | A2 | 11/1989 |
| ES | 2760470 | T3 | 5/2020 |
| GB | 2437549 | A | 10/2007 |
| GB | 2576743 | A | 3/2020 |
| JP | S49-75171 | A | 7/1974 |
| JP | S54-147066 | A | 11/1979 |
| JP | S58-190719 | A | 11/1983 |
| JP | S60-219517 | A | 11/1985 |
| JP | H02-057240 | B2 | 12/1990 |
| JP | H08-271301 | A | 10/1996 |
| JP | H10-104041 | A | 4/1998 |
| JP | 2007-303982 | A | 11/2007 |
| JP | 2008-524618 | A | 7/2008 |
| JP | 2009-068959 | A | 4/2009 |
| JP | 2010-121950 | A | 6/2010 |
| JP | 2010-530978 | A | 9/2010 |
| JP | 2012-105947 | A | 6/2012 |
| JP | 2012-225790 | A | 11/2012 |
| JP | 2018108356 | A | 7/2018 |
| KR | 20070115495 | A | 12/2007 |
| NL | 2013740 | A | 8/2016 |
| RU | 2615727 | C2 | 4/2017 |
| WO | 1981003427 | A1 | 12/1981 |
| WO | 2004045410 | A1 | 6/2004 |
| WO | 2013013782 | A2 | 1/2013 |
| WO | 20130178742 | A1 | 12/2013 |
| WO | 2014/043650 | A2 | 3/2014 |
| WO | 2014105755 | A1 | 7/2014 |
| WO | 2014108690 | A1 | 7/2014 |
| WO | 2014/135856 | A1 | 9/2014 |
| WO | 2014/151068 | A2 | 9/2014 |
| WO | 2014145971 | A2 | 9/2014 |
| WO | 201511402 | A1 | 1/2015 |
| WO | 2015/105916 | A1 | 7/2015 |
| WO | 2015/127390 | A1 | 8/2015 |
| WO | 2015191125 | A1 | 12/2015 |
| WO | 2016177901 | A1 | 11/2016 |
| WO | 2017/023794 | A1 | 2/2017 |
| WO | 2018156624 | A1 | 8/2018 |
| WO | 2019066357 | A1 | 4/2019 |
| WO | 2019106675 | A1 | 6/2019 |
| WO | 2019/226697 | A1 | 11/2019 |
| WO | 2020033752 | A1 | 2/2020 |
| WO | 2020154370 | A1 | 7/2020 |
| WO | 2020251893 | A1 | 12/2020 |
| WO | 2022108589 | A1 | 5/2022 |
| WO | 2022182794 | A1 | 9/2022 |
| WO | 2023022895 | A1 | 2/2023 |
| WO | 2023027871 | A1 | 3/2023 |
| WO | 2023076067 | A1 | 5/2023 |

OTHER PUBLICATIONS

U.S. Appl. No. 17/054,493, filed Nov. 10, 2020 Non-Final Office Action dated Jan. 27, 2023.
U.S. Appl. No. 17/262,080, filed Jan. 21, 2021 Non-Final Office Action dated Apr. 6, 2023.
U.S. Appl. No. 17/3026,821, filed May 3, 2021 Non-Final Office Action dated Jan. 10, 2023.
U.S. Appl. No. 17/373,535, filed Jul. 12, 2021 Non-Final Office Action dated Nov. 9, 2022.
U.S. Appl. No. 17/373,535, filed Jul. 12, 2021 Notice of Allowance dated Feb. 23, 2023.
U.S. Appl. No. 17/552,250, filed Dec. 15, 2021 Advisory Action dated May 8, 2025.
U.S. Appl. No. 17/552,250, filed Dec. 15, 2021 Notice of Allowance dated May 20, 2025.
U.S. Appl. No. 17/587,938, filed Jan. 28, 2022 Non-Final Office Action dated May 12, 2025.
U.S. Appl. No. 17/682,785, filed Feb. 28, 2022 Non-Final Office Action dated Jul. 16, 2025.
U.S. Appl. No. 17/833,682, filed Jun. 6, 2022 Final Office Action dated May 12, 2025.
U.S. Appl. No. 17/863,923, filed Jul. 13, 2022 Restriction Requirement dated May 21, 2025.
U.S. Appl. No. 17/870,698, filed Jul. 21, 2022 Final Office Action dated Jul. 29, 2025.
U.S. Appl. No. 17/873,834, filed Jul. 26, 2022 Non-Final Office Action dated May 19, 2025.
U.S. Appl. No. 17/879,658, filed Aug. 2, 2022 Final Office Action dated May 14, 2025.
U.S. Appl. No. 17/893,435, filed Aug. 23, 2022 Notice of Allowance dated Jul. 11, 2025.
U.S. Appl. No. 17/941,941, filed Sep. 9, 2022 Restriction Requirement dated May 28, 2025.
U.S. Appl. No. 18/036,335, filed May 10, 2023 Non-Final Office Action dated Jun. 18, 2025.
U.S. Appl. No. 18/278,167, filed Aug. 21, 2023 Non-Final Office Action dated Apr. 24, 2025.
U.S. Appl. No. 18/682,075, filed Feb. 7, 2024 Non-Final Office Action dated Jun. 18, 2025.
"Volumetric Flow Rate", www.vcalc.com/wiki/JeffNolumetric+%28Fluid%29+Flow+Rate, accessed Jan. 9, 2025, created Mar. 8, 2018 (Year: 2018).
U.S. Appl. No. 17/552,250, filed Dec. 15, 2021 Final Office Action dated Feb. 11, 2025.
U.S. Appl. No. 17/556,931, filed Dec. 20, 2021 Advisory Action dated Dec. 6, 2024.
U.S. Appl. No. 17/556,931, filed Dec. 20, 2021 Notice of Allowance dated Mar. 18, 2025.
U.S. Appl. No. 17/560,079, filed Dec. 22, 2021 Notice of Allowance dated Oct. 29. 2024.
U.S. Appl. No. 17/587,938, filed Jan. 28, 2022 Restriction Requirement dated Jan. 22, 2025.
U.S. Appl. No. 17/682,785, filed Feb. 28, 2022 Restriction Requirement dated Apr. 2, 2025.
U.S. Appl. No. 17/833,682, filed Jun. 6, 2022 Non-Final Office Action dated Jan. 15, 2025.
U.S. Appl. No. 17/863,223, filed Jul. 12, 2022 Non-Final Office Action dated Apr. 2, 2025.
U.S. Appl. No. 17/870,698, filed Jul. 21, 2022 Non-Final Office Action dated Apr. 9, 2025.
U.S. Appl. No. 17/870,698, filed Jul. 21, 2022 Restriction Requirement dated Feb. 12, 2025.

(56) References Cited

OTHER PUBLICATIONS

U.S. Appl. No. 17/879,658, filed Aug. 2, 2022 Non-Final Office Action dated Dec. 30, 2024.
U.S. Appl. No. 17/893,435, filed Aug. 23, 2022 Non-Final Office Action dated Jan. 17, 2025.
EP 20962628.2 filed May 31, 2023 Extended European Search Report dated Apr. 20, 2024.
EP 23188337.2 filed May 21, 2019 Extended European Search Report dated Dec. 4, 2023.
PCT/US2019/033389 filed Nov. 26, 2020 Extended European Search Report dated Jun. 4, 2021.
PCT/US2022/039191 filed Aug. 2, 2022 International Search Report and Written Opinion dated Dec. 5, 2022.
PCT/US2022/039746 filed Aug. 8, 2022 International Search Report and Written Opinion dated Nov. 18, 2022.
PCT/US2022/046920 filed Oct. 17, 2022 International Search Report and Written Opinion dated Feb. 20, 2023.
U.S. Appl. No. 17/054,493, filed Nov. 10, 2020 Notice of Allowance dated Jan. 4, 2024.
U.S. Appl. No. 17/306,821, filed May 3, 2021 Notice of Allowance dated Apr. 23, 2024.
U.S. Appl. No. 17/373,546, filed Jul. 12, 2021 Notice of Allowance dated Mar. 7, 2024.
U.S. Appl. No. 17/373,546, filed Jul. 12, 2021 Notice of Allowance dated May 29, 2024.
U.S. Appl. No. 17/556,907, filed Dec. 20, 2021 Notice of Allowance dated Dec. 6, 2023.
U.S. Appl. No. 17/556,931, filed Dec. 20, 2021 Non-Final Office Action dated Mar. 27, 2024.
U.S. Appl. No. 17/556,931, filed Dec. 20, 2021 Restriction Requirement dated Feb. 22, 2024.
"Urocare Reusable Night Drain Bottle—Urinary Collection System" Aug. 13, 2020, HealthProductsForYou.com, <https://www.healthproductsforyou.com/p-urocare-reusable-night-drain-bottle-urinary-collection-system.html> retrieved from Archive.org (Year: 2020).
U.S. Appl. No. 17/552,250, filed Dec. 15, 2021 Non-Final Office Action dated Sep. 19, 2024.
U.S. Appl. No. 17/556,931, filed Dec. 20, 2021 Final Office Action dated Oct. 1, 2024.
Bard Medical, Criticore Disposables—Non I.C., 3 pages, www.bardmedical.com/products/patienl-moniloring-,ystems/criticore®-system/criticore®-disposables-non-ic/ Jan. 30, 2015.
Bard Medical, Criticore Infection Control Disposables, 3 pages, www.bardmedical.com/patienl-moniloring-,ystems/criticore®-system/criticore®-infection-control-disposables/ Jan. 30, 2015.
Bard Medical, Criticore Monitor, 11 pages, www.bardmedical.com/products/patient-monitoring-systems/criticore®--monitor/ Jan. 30, 2015.
Bard Medical, Urine Meiers, 3 pages, www.bardmedical.com/products/urological-drainage/urine-collection/urinemeters/Jan. 30, 2015.
Biometrix, Urimetrix, 4 pages, www.biometrixmedical.com/Products/56/Urimetrix%E2%84%A2 Oct. 29, 2014.
Observe Medical, sippi, 3 pages, www.observemedical.com/products.html Oct. 29, 2014.
PCT/US19/33389 filed May 21, 2019 International Search Report and Written Opinion dated Aug. 2, 2019.
PCT/US2016/044835 filed Jul. 20, 2016 International Search Report and Written Opinion dated Dec. 16, 2016.
PCT/US2019/045787 filed Aug. 8, 2019 International Preliminary Report on Patentability dated Feb. 16, 2021.
PCT/US2019/045787 filed Aug. 8, 2019 International Search Report and Written Opinion dated Oct. 2, 2019.
U.S. Appl. No. 15/748,107, filed Jan. 26, 2018 Final Office Action dated Dec. 23, 2020.
U.S. Appl. No. 15/748,107, filed Jan. 26, 2018 Final Office Action dated Feb. 7, 2022.
U.S. Appl. No. 15/748,107, filed Jan. 26, 2018 Non-Final Office Action dated Sep. 3, 2021.
U.S. Appl. No. 15/748,107, filed Jan. 26, 2018 Non-Final Office Action dated Sep. 4, 2020.
U.S. Appl. No. 17/054,493, filed Nov. 10, 2020 Final Office Action dated May 31, 2022.
U.S. Appl. No. 17/054,493, filed Nov. 10, 2020 Non-Final Office Action dated Nov. 24, 2021.
DFree Personal—Consumer Product Brochure, 2019.
DFree Pro Brochure 2019.
Leonhäuser, D et al., "Evaluation of electrical impedance tomography for determination of urinary bladder volume: comparison with standard ultrasound methods in healthy volunteers."—BioMed Engr On-line; 17:95; 2018.
Li, R., et al., "Design of a Noninvasive Bladder Urinary Volume Monitoring System Based on Bio-Impedance."—Engineering; vol. 5; pp. 321-325; 2013.
PCT/US20/61367 filed Nov. 19, 2020 International Search Report and Written Opinion dated Feb. 22, 2021.
PCT/US2022/017574 filed Feb. 23, 2022 Internation Search Report and Written Opinion dated Jun. 8, 2022.
Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper; Mar. 2020.
Schlebusch, T. et al., "Bladder volume estimation from electrical impedance tomography" Physiological Measurement, Institute of Physics, Bristol, GB. vol. 35 No. 9 Aug. 20, 2014. (Aug. 20, 2014).
SECA product catalog, https://us.secashop.com/products/seca-mbca/seca-mbca-514/5141321139, last accessed Sep. 11, 2020.
U.S. Appl. No. 17/054,493, filed Nov. 10, 2020 Final Office Action dated Oct. 4, 2023.
U.S. Appl. No. 17/262,080, filed Jan. 21, 2021 Final Office Action dated Sep. 11, 2023.
U.S. Appl. No. 17/262,080, filed Jan. 21, 2021 Notice of Allowance dated Oct. 13, 2023.
U.S. Appl. No. 17/306,821, filed May 3, 2021 Advisory Action dated Oct. 3, 2023.
U.S. Appl. No. 17/306,821, filed May 3, 2021 Final Office Action dated Jul. 19, 2023.
U.S. Appl. No. 17/373,546, filed Jul. 12, 2021 Non-Final Office Action dated Nov. 1, 2023.
U.S. Appl. No. 17/556,907, filed Dec. 20, 2021 Non-Final Office Action dated Aug. 17, 2023.
U.S. Appl. No. 17/556,907, filed Dec. 20, 2021 Restriction Requirement dated May 12, 2023.
U.S. Appl. No. 17/833,682, filed Jun. 6, 2022 Non-Final Office Action dated Sep. 15, 2025.
U.S. Appl. No. 17/863,223, filed Jul. 12, 2022 Advisory Action dated Dec. 1, 2025.
U.S. Appl. No. 17/863,223, filed Jul. 12, 2022 Final Office Action dated Sep. 24, 2025.
U.S. Appl. No. 17/863,923, filed Jul. 13, 2022 Non-Final Office Action dated Oct. 22, 2025.
U.S. Appl. No. 17/870,698, filed Jul. 21, 2022 Non-Final Office Action dated Nov. 21, 2025.
U.S. Appl. No. 17/873,834, filed Jul. 26, 2022 Final Office Action dated Nov. 28, 2025.
U.S. Appl. No. 17/879,658, filed Aug. 2, 2022 Non-Final Office Action dated Nov. 18, 2025.
U.S. Appl. No. 17/941,941, filed Sep. 9, 2022 Non-Final Office Action dated Aug. 22, 2025.
U.S. Appl. No. 18/036,335, filed May 10, 2023 Notice of Allowance dated Oct. 21, 2025.
U.S. Appl. No. 18/278,167, filed Aug. 21, 2023 Notice of Allowance dated Oct. 16, 2025.
Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, accessed Sep. 10, 2025 (Year: 2021).
Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, translated via Google Translate, accessed Sep. 10, 2025 (Year:2025).

(56) References Cited

OTHER PUBLICATIONS

U.S. Appl. No. 17/682,785, filed Feb. 28, 2022 Final Office Action dated Jan. 9, 2026.
U.S. Appl. No. 17/833,682, filed Jun. 6, 2022 Advisory Action dated Mar. 24, 2026.
U.S. Appl. No. 17/833,682, filed Jun. 6, 2022 Final Office Action dated Jan. 16, 2026.
U.S. Appl. No. 17/863,923, filed Jul. 13, 2022 Notice of Allowance dated Feb. 27, 2026.
U.S. Appl. No. 17/873,834, filed Jul. 26, 2022 Advisory Action dated Jan. 30, 2026.
U.S. Appl. No. 17/873,834, filed Jul. 26, 2022 Non-Final Office Action dated Mar. 12, 2026.
U.S. Appl. No. 17/941,941, filed Sep. 9, 2022 Advisory Action dated Apr. 7, 2026.
U.S. Appl. No. 17/941,941, filed Sep. 9, 2022 Final Office Action dated Jan. 30, 2026.
U.S. Appl. No. 18/612,745, filed Mar. 21, 2024 Non-Final Office Action dated Apr. 1, 2026.
U.S. Appl. No. 18/682,075, filed Feb. 7, 2024 Advisory Action dated Mar. 6, 2026.
U.S. Appl. No. 18/682,082, filed Feb. 7, 2024 Non-Final Office Action dated Feb. 11, 2026.
U.S. Appl. No. 18/701,916, filed Apr. 16, 2024 Non-Final Office Action dated Mar. 23, 2026.
Wilson NPL SWIR Imaging 101 https://~wilson.com/swir-imaging-101-what-can-it-do-for-you/ Jan. 2021 (Year: 2021).
U.S. Appl. No. 17/682,785, filed Feb. 28, 2022 Notice of Allowance dated Jun. 30, 2026.
U.S. Appl. No. 17/863,223, filed Jul. 12, 2022 Non-Final Office Action dated Apr. 21, 2026.
U.S. Appl. No. 17/870,698, filed Jul. 21, 2022 Final Office Action dated Jun. 17, 2026.
U.S. Appl. No. 17/879,658, filed Aug. 2, 2022 Final Office Action dated Apr. 24, 2026.
U.S. Appl. No. 17/941,941, filed Sep. 9, 2022 Non-Final Office Action dated Jun. 25, 2026.
U.S. Appl. No. 18/538,136 filed Dec. 13, 2023 Restriction Requirement dated May 14, 2026.
U.S. Appl. No. 18/682,082, filed Feb. 7, 2024 Final Office Action dated Jun. 11, 2026.
U.S. Appl. No. 18/765,516, filed Jul. 8, 2024 Non-Final Office Action dated May 21, 2026.

* cited by examiner

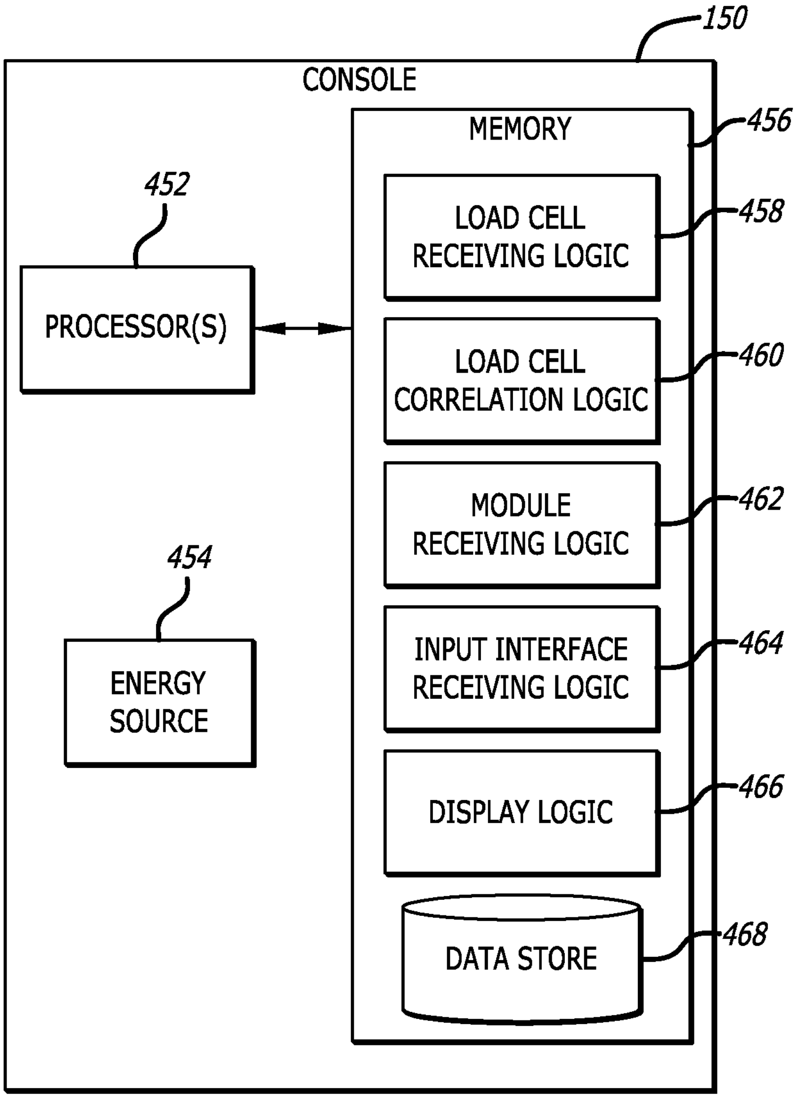
FIG. 4
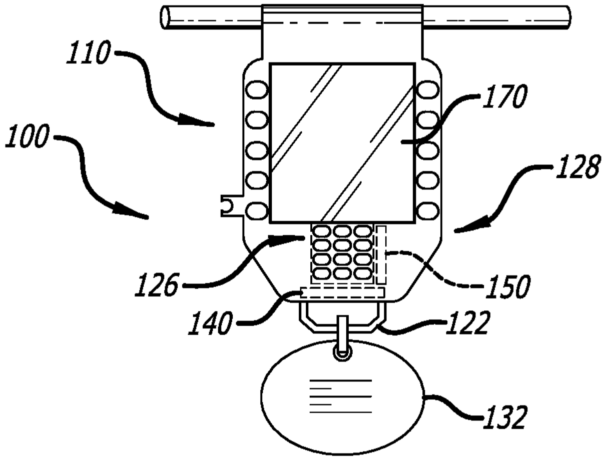

AUTOMATED URINARY OUTPUT MEASURING SYSTEM

PRIORITY

This application claims the benefit of priority to U.S. Provisional Application No. 63/237,085, filed Aug. 25, 2021, which is incorporated by reference in its entirety into this application.

BACKGROUND

Some current urine monitoring systems use weight based methodologies to determine urine volume and urine flow rate over time. A fluid collection container may be suspended from a weighing device and as urine is captured by the fluid collection container, the weight of the fluid collection container increases. The weighing device may be configured to detect the increase in the weight of the fluid collection container. However, most urine monitoring systems do not travel with a patient as the patient is moved through a hospital setting, requiring clinicians to suspend urine monitoring until a patient is stationed in one location. If a patient has to move frequently within the hospital (e.g., multiple surgeries), critical patient data may not be captured. It would be beneficial to the patient and the clinician to be able to monitor urine output during the patient's entire stay. Disclosed herein is an automated urinary output monitoring system and method of use that address the foregoing.

SUMMARY

Disclosed herein is an automated urinary output monitoring system including an automated urinary output monitoring device. The device includes a device body having a mounting system coupled thereto. The mounting system includes a mounting surface rotatably coupled with the device body, where the mounting surface is configured to secure the automated urinary output monitoring device to an external stabilizing surface. The mounting system further includes a buffering region disposed between the mounting surface and the device body, where the buffering region is configured to isolate the device body from vibrations of the external stabilizing surface. The device further includes a load cell assembly operatively coupled with the device body having a fluid collection bag attachment coupled therewith, where the fluid collection bag attachment is configured to suspend a fluid collection bag therefrom.

The system further includes a console communicatively coupled with the load cell assembly, where the console including one or more processors, and non-transitory computer readable medium having logic stored thereon that, when executed by the one or more processors, performs operations of the system. The operations include (i) receiving a load value applied to the fluid collection bag attachment by the fluid collection bag, (ii) calculating a volume of urine collected within the fluid collection bag based on the load value, and (iii) depicting the volume of urine on a display of the system.

In some embodiments, the mounting system extends laterally away from a back panel of the device body. In some embodiments, the mounting surface includes a number of suction cups, clamps, magnets, or an adhesive configured for securing the mounting surface to the stabilizing surface. In some embodiments, the automated urinary output monitoring device is configured to rotate with respect to the mounting surface due to gravity to maintain a vertical orientation of the device body during use.

In some embodiments, the buffering region is configured to transition between a non-compressed configuration and a compressed configuration in response to a lateral movement of the stabilizing surface. In some embodiments, the mounting surface rotates about an axis of rotation extending through the buffering region.

In some embodiments, the automated urinary output monitoring device includes a front panel including the display and an input interface, where each are in communication with the console. In some embodiments, the input interface includes a plurality of buttons.

In some embodiments, the automated urinary output monitoring device includes one or more module inputs configured to define communication between one or more modules and the console.

In some embodiments, the system receives electrical power from an external power source.

In some embodiments, the operations further include correlating the volume of urine with a time of day and depicting the time of day along with the volume of urine on the display of the system.

In some embodiments, the automated urinary output monitoring device includes a tube holder coupled with the device body, where the tube holder is configured to secure a portion of a drainage tube of the fluid collection bag to the device body.

In some embodiments, the one or more modules includes a temperature sensor coupled with the tube holder, where the temperature sensor is configured to determine a temperature of urine disposed with in the drainage tube, and the operations further include obtaining a temperature measurement of the urine disposed with in the drainage tube and depicting the temperature measurement on the display.

In some embodiments, the automated urinary output monitoring device includes the securing attachment extending upward away from a top side of the device body, where the securing attachment is configured to suspend the automated urinary output monitoring device from a bed rail.

In some embodiments, the console is configured to wirelessly communicate with an external computing device, where the external computing device includes one or more of a tablet, a cell phone, or an electronic medical record (EMR) system, and the operations further include at least one of (i) receiving patient information from the external computing device or (ii) transmitting urine output monitoring data to the external computing device.

In some embodiments, the operations further include receiving a plurality of patient profiles from the EMR system and storing the plurality of the patient profiles on the non-transitory computer readable medium.

In some embodiments, the operations further include depicting patient profile information on the display.

Also disclosed herein is a method of monitoring urine output from a patient performed by a urine output monitoring system. According to some embodiments, the method includes (i) rotating a device body of the urine output monitoring system about an axis of rotation with respect to a mounting surface of the urine output monitoring system so that the device body is vertically oriented; (ii) obtaining a load value from a load cell assembly of the urine output monitoring system, where the load value is defined by a urine collection bag coupled with load cell assembly and the urine collection bag includes a volume of urine collected therein; (iii) calculating the volume of urine based on the load value; (iv) correlating the volume of urine with a time of day; (v) receiving patient identification for the patient from an EMR system; and (vi) depicting the volume of urine, the time of day, and the patient identification on a display of the urine output monitoring system.

In some embodiments, the method further includes transmitting the volume of urine, the time of day, and the patient identification to the EMR system.

In some embodiments, the method further includes obtaining a temperature measurement of the urine disposed within a drainage tube of the urine output monitoring system and depicting the temperature measurement on the display.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 4 illustrates a block diagram of some components of the system of FIG. 1 including a console, in accordance with some embodiments.

DESCRIPTION

Figure 1:
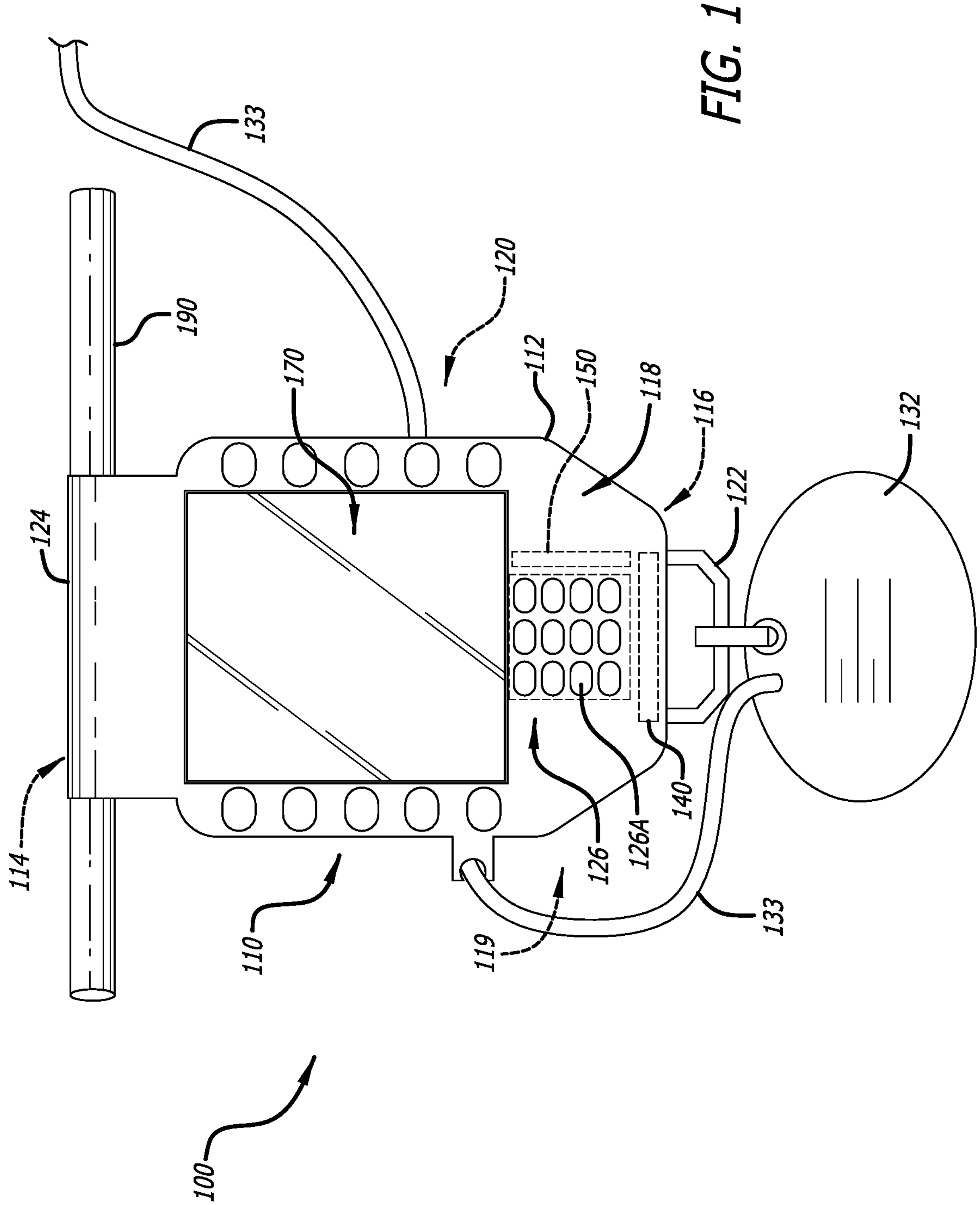
FIG. 1 illustrates a plan view of an automated urinary output measuring system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

Unless defined otherwise, all technical and scientific terms used herein have the same meaning as commonly understood by those of ordinary skill in the art.

FIG. 1 illustrates a perspective view of an automated urinary output measuring system 100, in accordance with some embodiments. The automated urinary output monitoring system (system) 100 includes the automated urinary output monitoring device (device) 110 having a device body 112 including a top side 114, a bottom side 116, a front panel 118, and a back panel 120. The device 110 includes a fluid collection bag attachment 122 extending downward from the device body 112, i.e., downward away from the bottom side 116. In some embodiments, the system 100 also includes a fluid collection bag 132 configured for coupling to the fluid collection bag attachment 122 during use. During use, the fluid collection bag 132 may be in fluid communication with a urinary catheter via a drainage tube 133 and collect a volume of fluid (urine) therein by gravity flow, negative pressure flow, or the like. The fluid collection bag 132 may be directly coupled to the fluid collection bag attachment 122 or may be coupled to the fluid collection bag attachment 122 via an intermediate device, such as a hook, a ring, or the like. The fluid collection bag 132 is coupled to the fluid collection bag attachment 122 so that any volume of fluid (urine) within the fluid collection bag 132 or any increase in volume of fluid within the fluid collection bag 132 defines a load (e.g., a hanging load) on the fluid collection bag attachment 122. The device 110 further includes a load cell assembly 140 configured to measure the load on the fluid collection bag attachment 122.

The load cell assembly 140 may be integrated into the bottom side 116 of the device 110 or may be located within the device body 112. The load cell assembly 140 is communicatively coupled with a console 150 of the system 100 wherein the load cell assembly 140 is configured to communicate load cell values (measurements) to the console 150. The load cell assembly 140 may be wired to the console 150 or may be wirelessly coupled with the console 150. The console 150 may reside within the device body 112. In some embodiments, the console 150 may be in wireless communication with an external computing device (e.g., a stand-a-alone computer, a tablet, or cell phone) or electronic medical record (EMR) system so that the console 150 may transmit load cell values to the computing device or the EMR system. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like.

The front panel 118 of the device 110 may include a display 170 integrated into or coupled to the device body 112. The display 170 may be in communication with the console 150 and may be configured to display determined load cell values or other information pertaining the monitoring of urine output. In some embodiments, the front panel 118 of the device 110 may include an input interface 126 in communication with the console 150. In some embodiments, the input interface 126 may include a plurality of buttons 126A configured to allow a user to input information into the system 100 and/or select information to be projected on the display 170. In some embodiments, the plurality of buttons 126A may be organized into a keypad array, positioned around the display 170, or a combination thereof.

The device 110 includes a securing attachment 124 configured to detachably couple the device 110 to a stabilizing surface 190. In some embodiments, the stabilizing surface 190 may include a rail of a hospital bed, an IV pole or the like. In some embodiments, the securing attachment 124 may include a hook, a clamp, or the like. The securing attachment 124 may be configured to allow the device 110 to be suspended from (i.e., hung from) the stabilizing surface 190 so that the device 110 is disposed in a vertical orientation, where the vertical orientation enables the load cell assembly 140 to precisely determine load values applied to the fluid collection bag attachment 122.

Figure 2:
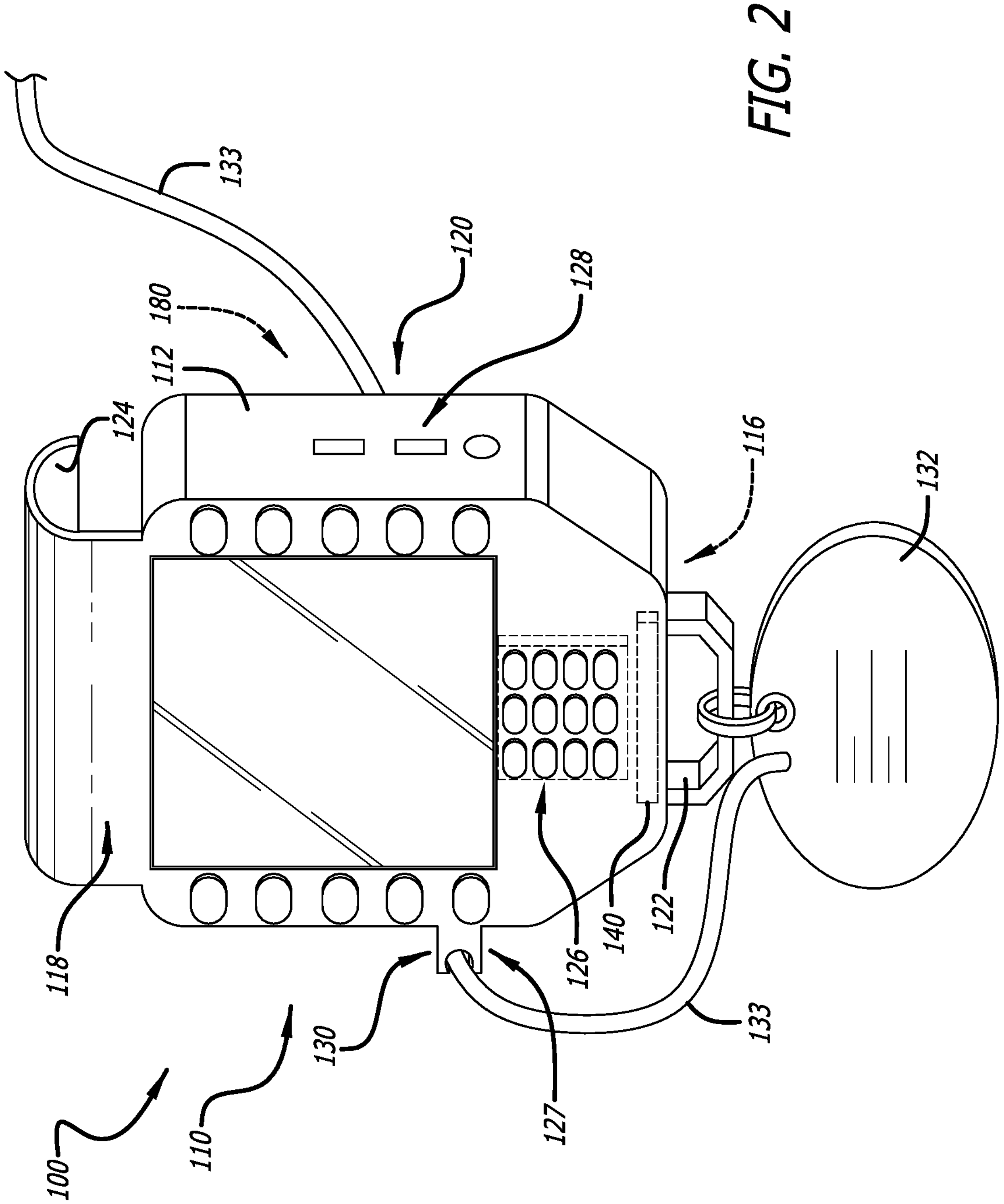
FIG. 2 illustrates a perspective view of the system of FIG. 1, in accordance with some embodiments.

FIG. 2 illustrates a perspective view of the automated urinary output measuring device 110, in accordance with some embodiments. In some embodiments, the device body 112 may include one or more module inputs 128 located on one or more sides of the device body 112. In some embodiments, the module inputs 128 may be configured to receive therein or otherwise couple with one or more modules, where the one or more modules may be configured to provide additional functionality to the system 100.

The device 110 may include a tube holder 130 configured for securing a portion of drainage tube 133 to the body 112. The tube holder 130 may be configured to optimally position and hold a drainage tube 133 so that movement of the patient does not affect the load applied to the fluid collection bag attachment 122. If the drainage tube is not adequately positioned and secured, the shape or strain of the drainage tube 1330 may alter the load obtained by the load cell assembly 140, confounding the determination of load cell values.

In some embodiments, the one or more modules may include a temperature sensor 127 coupled with the tube holder 130. The temperature sensor 127 may be configured to determine the temperature of the volume of fluid as the volume of fluid moves through the drainage tube 133 to the fluid collection bag 132.

In some embodiments, the fluid collection bag attachment 122 being fixed to the bottom side 116 of the device body 112 or the fluid collection bag attachment 122 be integrated into or formed into the device body 112. In some embodiments, the fluid collection bag attachment 122 is fixed directly underneath the device body 112, equidistant between the front panel 118 and the back panel 120. The fluid collection bag attachment 122 and the device body 112 may be formed as a single piece. In some embodiments, the device body 112 and the fluid collection bag attachment 122 may be formed of a thermoplastic material (e.g., polyvinyl chloride, polyethylene, polypropylene, polystyrene, polyurethane, nylon, or any other suitable thermoplastic material) formed by 3D printing, injection molding or the like. Advantageously, the device body 112 and the fluid collection bag attachment 122 being formed as a singular piece removes attachment/reattachment of the fluid collection bag attachment 122 and rotation of the fluid collection bag 132 around the fluid collection bag attachment 122, leading to longevity of the device 110 and consistency of the load cell assembly 140 detecting the load of the fluid collection bag attachment 122. In an embodiment, the load cell assembly 140 may be integrated into the fluid collection bag attachment 122. Advantageously, fixing the fluid collection bag attachment 122 to the device body 112 ensures both consistent placement of the fluid collection bag 132 on the fluid collection bag attachment 122 and that the load cell assembly 140 is protected and consistently able to transmit load values to the console 150 during multiple deployments of the system 100 or multiple changes of the fluid collection bag 132.

Figure 3A:
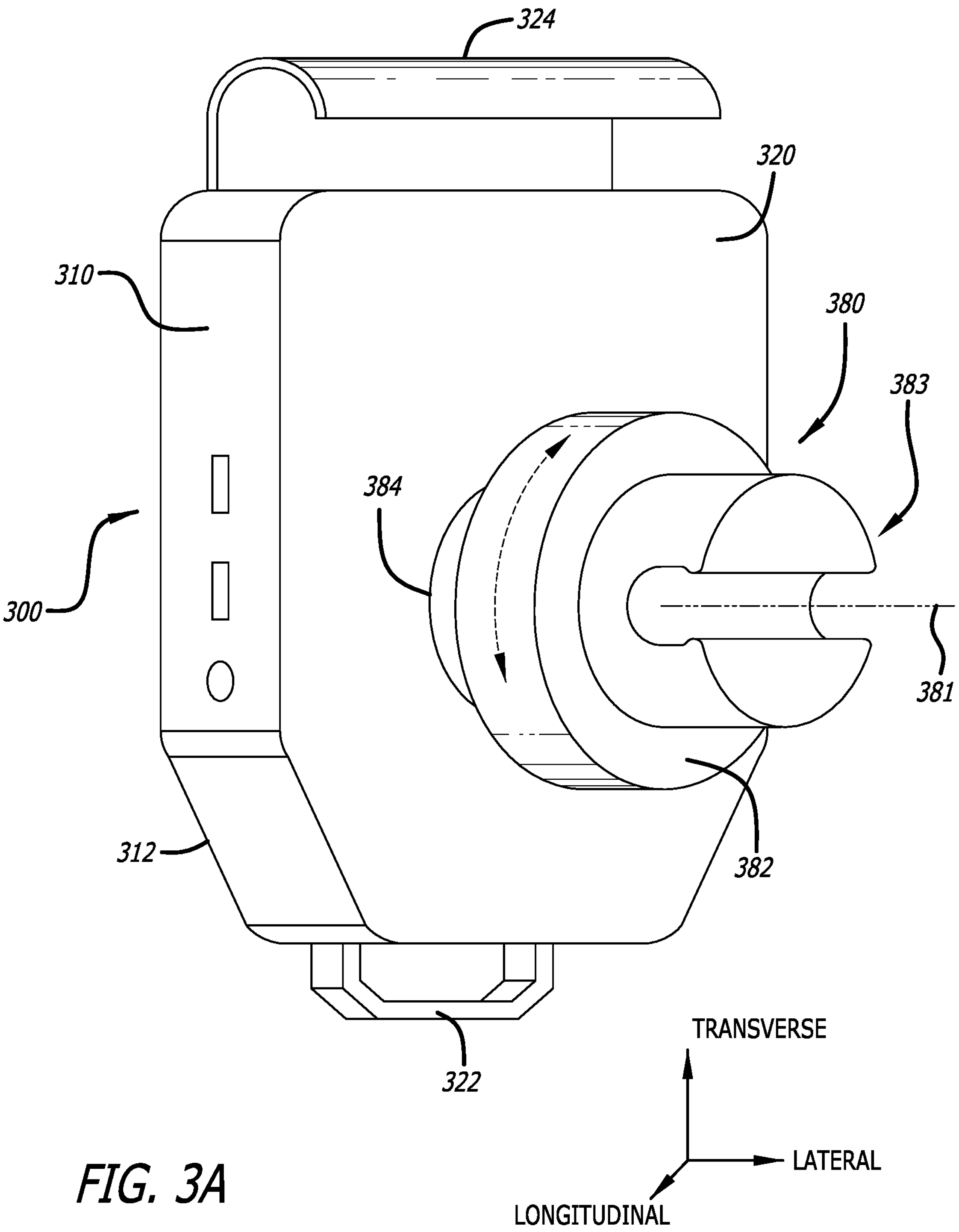
FIG. 3A illustrates perspective view of a back panel of another embodiment of an automated urinary output measuring system, in accordance with some embodiments.
Figure 3C:
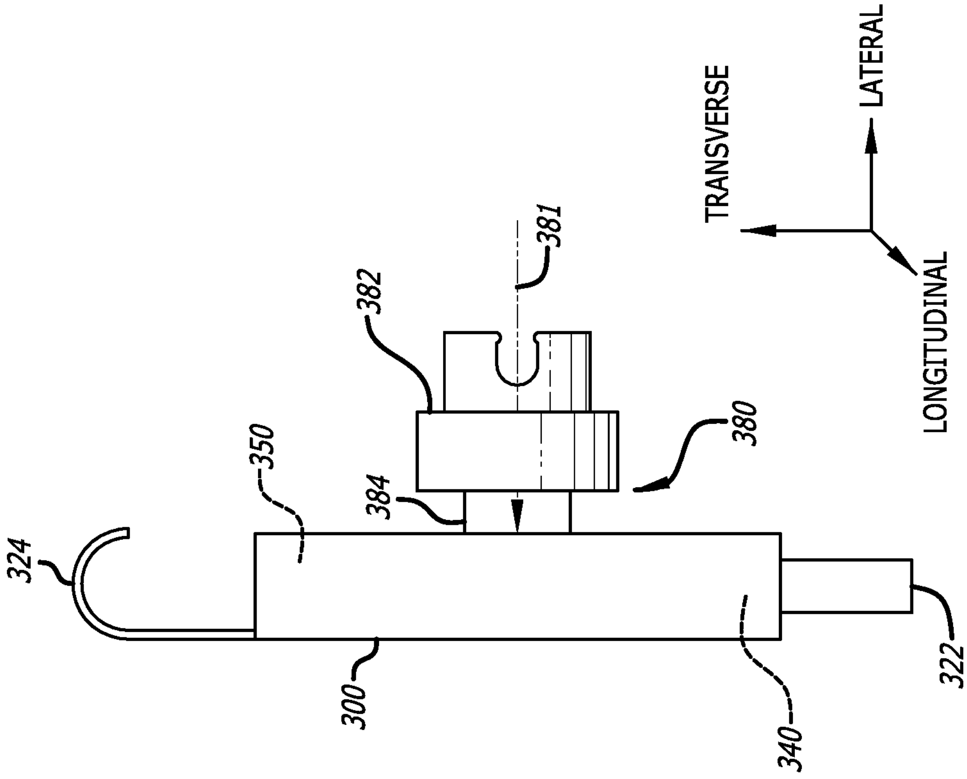
FIGS. 3B-3C illustrate a side view of the automated urinary output measuring device of FIG. 3A including a mounting system, in accordance with some embodiments.
Figure 3B:
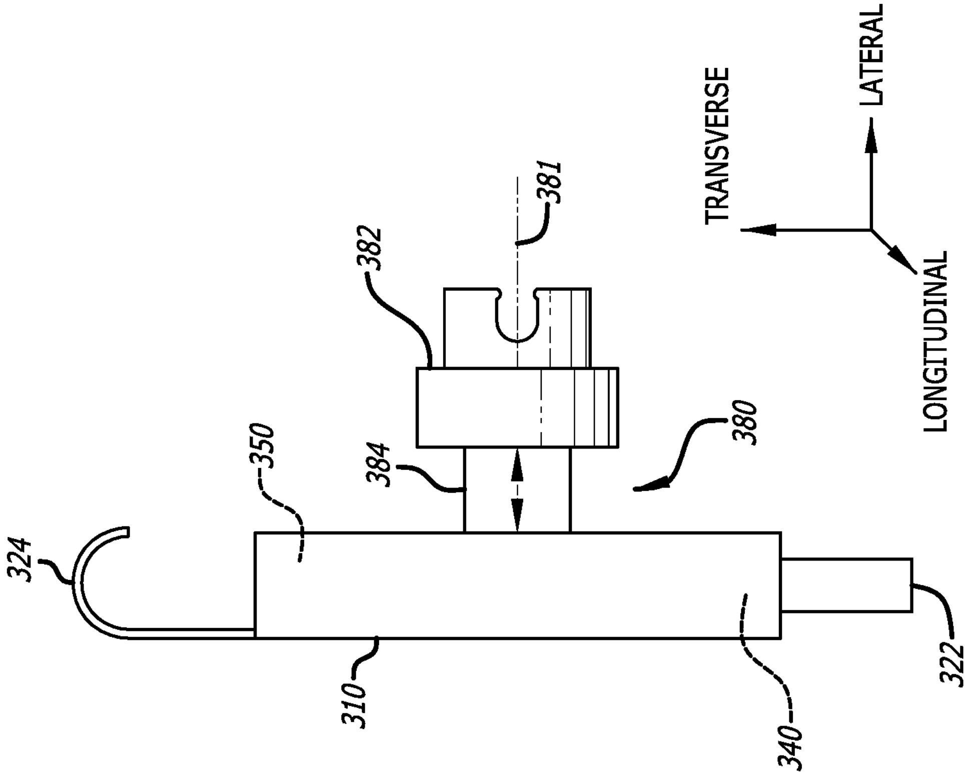

FIGS. 3A-3C illustrate another embodiment of automated urinary output measuring system 300 that can, in certain respects, resemble components of the automated urinary output measuring system 100 described in connection with FIGS. 1-2. It will be appreciated that all the illustrated embodiments may have analogous features. Accordingly, like features are designated with like reference numerals, having leading digits of "3." For instance, the device is designated as "110" in FIGS. 1-2, and an analogous device is designated as "310" in FIGS. 3A-3C. Relevant disclosure set forth above regarding similarly identified features thus may not be repeated hereafter. Moreover, specific features of the automated urinary output measuring system 100 and related components shown in FIGS. 1-2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the automated urinary output measuring system of FIGS. 3A-3C. Any suitable combination of the features, and variations of the same, described with respect to the coronary automated urinary output measuring system 100 and components illustrated in FIGS. 1-2 can be employed with the automated urinary output measuring system and components of FIGS. 3A-3C, and vice versa.

FIG. 3A illustrates a perspective view of the back panel 320 of the automated urinary output measuring device 310, in accordance with some embodiments. The back panel 320 of the device 310 includes a mounting system 380 configured to allow the device 310 to hang vertically when an orientation of the stabilizing surface 190 is oriented away from a horizontal orientation. For example, the mounting system 380 may facilitate accurate measurement of urine output when the position of the patient is adjusted, such as between a lying position and a sitting position, for example. The mounting system 380 configured facilitate rotation of a mounting surface 382 with respect to the body 312 of the device 310 about an axis 381 so that the device 310 maintains a vertical orientation when the orientation of the stabilizing surface 190 is rotated away from a horizontal orientation. Similar to the securing attachment 324, mounting surface 382 is configured to couple the device 310 to the stabilizing surface 190 (see FIG. 1). In some instances, some stabilizing surfaces 190 (e.g., hospital beds or the like) may have portions of the stabilizing surfaces 190 that change orientation, forcing a device hung by the securing attachment 324 to be removed from the stabilizing surface 190 and to be repositioned to ensure the device 310 remains vertically oriented.

The mounting system 380 couples the device 310 to the stabilizing surface 190 along the axis 381. In some embodiments, the mounting system 380 extends laterally from a back panel 320 of the device 310. During use, the device 310 may be coupled to the stabilizing surface 190 via the securing attachment 324, the mounting system 380, or a combination thereof. In some embodiments, the stabilizing surface 190 be flat or may include portions of a hospital bed, a wall, an IV stand, a bed pole mount, or the like. In some embodiments, the mounting surface 382 may include a mounting mechanism 383 that may include a number (e.g., 1, 2, 3, 4 or more) of suction cups, clamps or magnets. In some embodiments, portions of the mounting surface 382 may include an adhesive configured to secure the mounting system 380 to the stabilizing surface 190. The mounting system 380 may be configured to prevent any sag or rotation of the device 310 except about the axis 381.

The mounting system 380 may also be configured to isolate the load cell system 340 from vibrations of the stabilizing surface 190. The mounting system 380 may include a buffering region 384 disposed between the back panel 320 and the mounting surface 382. The mounting surface 382 may be configured to couple the device 310 to a surface, including the stabilizing surface 190. Advantageously, the mounting surface 382 positions the device 310 to maintain the device in the vertical orientation so the fluid collection bag attachment 322 is suspended in line with the load cell assembly 340 and so that the stability of the device 310 in enhanced, e.g., isolated from vibrational movement of the stabilizing surface 190.

In some embodiments, the buffering region 384 buffers lateral movement of the device 310. In some embodiments, the buffering region 384 may include a spring. In some embodiments, the buffering region 384 may include a damping material such as a rubber or foam material. In some embodiments, the buffering region 384 may also be configured to allows the device 310 to move or rotate axially around the axis 381, allowing the device 310 to be maintained in a vertical orientation regardless of the orientation of the stabilizing surface 190. In some embodiments, the buffering region 384 may be configured (e.g., include stops) to limit rotation of the device 310 around the axis 381. In some embodiments, the user or the weight of the fluid collection bag 132 (see FIGS. 1-2) coupled to the fluid collection bag attachment 322 may rotate the device body 312 axially around the axis 381 to the vertical orientation, as will be described in more detail herein.

FIGS. 3B-3C illustrate a side view of the device 310 including the mounting system 380. In some embodiments, the mounting system 380 may be configured to transition between a non-compressed configuration and a compressed configuration to buffer lateral movement of the device 310. As illustrated in FIG. 3B, in the non-compressed configuration, the buffering region 384 may be fully extended away from the device 310 along the lateral axis. As illustrated in FIG. 3C, in the compressed configuration, the buffering region 384 may be partially or fully compressed toward the device 310 along the axis 381. In some embodiments, the buffering region 384 may collapse upon itself or may laterally slide into the mounting surface 382. The mounting system 380 may transition between the non-compressed configuration and the compressed configuration due to vibrations or sudden lateral movement of the stabilizing surface 190 with respect to the mounting surface 382. While the mounting system 380 is in the non-compressed configuration or the compressed configuration, the device may be rotated about the axis 381. Advantageously, the mounting system 380 stabilizes the device 310 during lateral movement, positions the device 310 in the vertical orientation, and buffers the device 310 from lateral movement impacting the ability of the load cell assembly 340 to determine load values.

In some embodiments, the device 310 may include an accelerometer (not shown) located within the device 310 that may be configured to determine the orientation of the device 310. The accelerometer may be in communication with the console 350 so as to receive accelerometer values from the accelerometer, where the console 350 may use the accelerometer values adjust load values obtained by the load cell assembly 340 to enhance the measurement accuracy of the load applied to the load cell assembly 340 and calculate the volume of fluid within the fluid collection bag 132 taking into account the orientation of the device 310. In some embodiments, the device 310 may include a gyroscope (not shown) that may be configured to stabilize the load cell assembly 340, such as maintain the device 310 in the vertical orientation and/or inhibit vibrations of the device 310 from affecting the ability of the load cell assembly 340 to detect load cell values. In some embodiments, the FIG. 4 illustrates a block diagram of some components of the system 100 including the console 150, in accordance with some embodiments. In some embodiments, the console 150 may include one or more processors 452, an energy source 454, non-transitory computer readable medium ("memory") 456 and a plurality of logic modules. In some embodiments, the energy source 454 may be configured to provide power to the display 170 and the load cell assembly 140. In some embodiments, the energy source 154 may include an external power source. In some embodiments, wherein the external power source 154 is not connected to the console, the console 150, the display 170 and the load cell assembly 140 may not be operable.

For illustrative purposes, logic of the console 150 may be divided into a number of logic modules that may include load cell receiving logic 458, load cell correlation logic 460, module receiving logic 462, input interface receiving logic 464, display logic 466, and a data store 468.

The load cell receiving logic 458 may generally be configured to receive electrical signals (i.e., load cell values) from the load cell assembly 140. In some embodiments, the load cell receiving logic 458 may be configured to constantly (e.g., at a high sampling rate) receive the load cell values. In some embodiments, the sampling rate may be defined by the user, such as a sampling rate of every 5 minutes for example. In some embodiments, the load cell receiving logic 458 may be configured to receive the load cell values upon a defined change or difference from a previous load cell values.

The load cell correlation logic 460 may be configured to correlate the received load cell value with a volume of urine collected within the fluid collection bag 132. In some embodiments, the load cell correlation logic 460 may be configured correlate the volume of urine with a time of day value. In other words, the load cell correlation logic 460 may attach time stamp to each the volume of urine. By way of summary, a volume of urine may be calculated for each load cell value, and each volume of urine may include an attached time stamp.

The module receiving logic 462 may be configured to receive data from any of the one or more modules coupled with module inputs 128. The module receiving logic 462 may also be configured to receive data wirelessly from an external source, such as the external computing device or the EMR system. For example, the module receiving logic 462 may receive patient identification information from the EMR system and the volume of urine values to a specific patient. In some embodiments, the module receiving logic 462 may receive patient identification information for a plurality of patients and the patient information may be stored in the data store 468. The module receiving logic 462 may also be configured to receive/obtain temperature data from the temperature sensor 127 and correlate the temperature data with the volume of urine values.

In some embodiments, the input interface receiving logic 464 may be configured to receive input from the user via the input interface 126 including the plurality of buttons 126A. The input interface receiving logic 464 may, in response to the input, change a mode of operation, such as change the load cell sampling rate, for example. The user may also input various settings, such as a volume capacity for the fluid collection bag 132. The user may also define a number of alert limits for the system, such as a leak alert associated in a decrease in load cell values, or a low urine output rate, for example.

In some embodiments, the display logic 466 may be configured to project urine output information on the display 170, such as the determined load cell values, the correlated volume values, the time of day values, the patient identification information, the urine temperature data, and/or module data from the one or more modules. The display logic 466 may also be configured to transmit the urine output information to the external computing device or the EMR system.

In some embodiments, the data store 468 may be configured to store the detected load cell values, the correlated volume values, the time of day values, and the module data values. The data store 468 may be configured to store multiple patient profiles as may be input by the user or received from the EMR system. In some embodiments, the data store 468 may be configured to record and store all data received, generated, obtained, or otherwise utilized by the system 100.

Figure 5A:
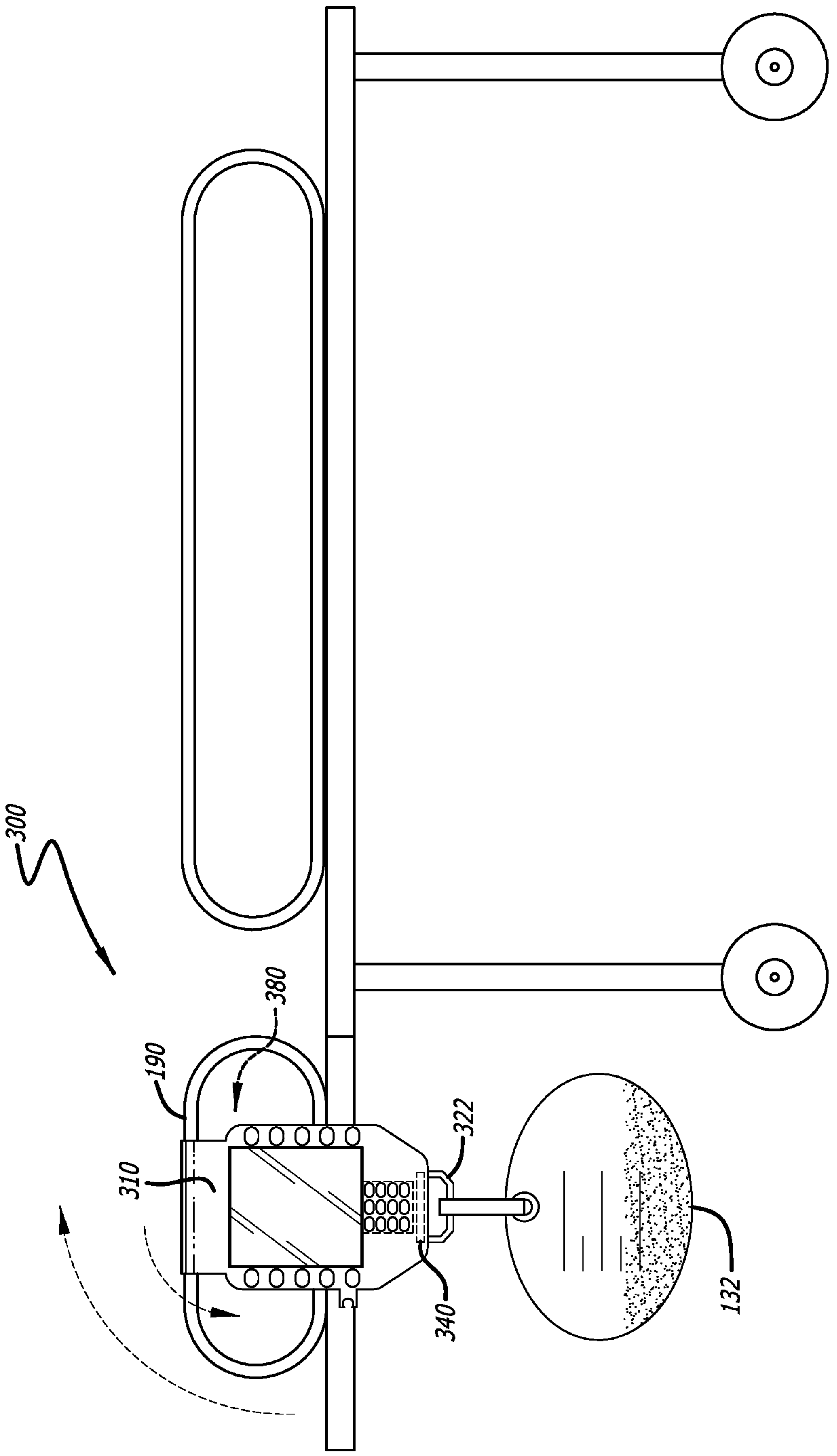
FIGS. 5A-5B illustrates a perspective view of the system of FIG. 3A depicting an exemplary method of the mounting system maintaining the automated urinary output measuring system in a vertical orientation, in accordance with some embodiments.
Figure 5B:
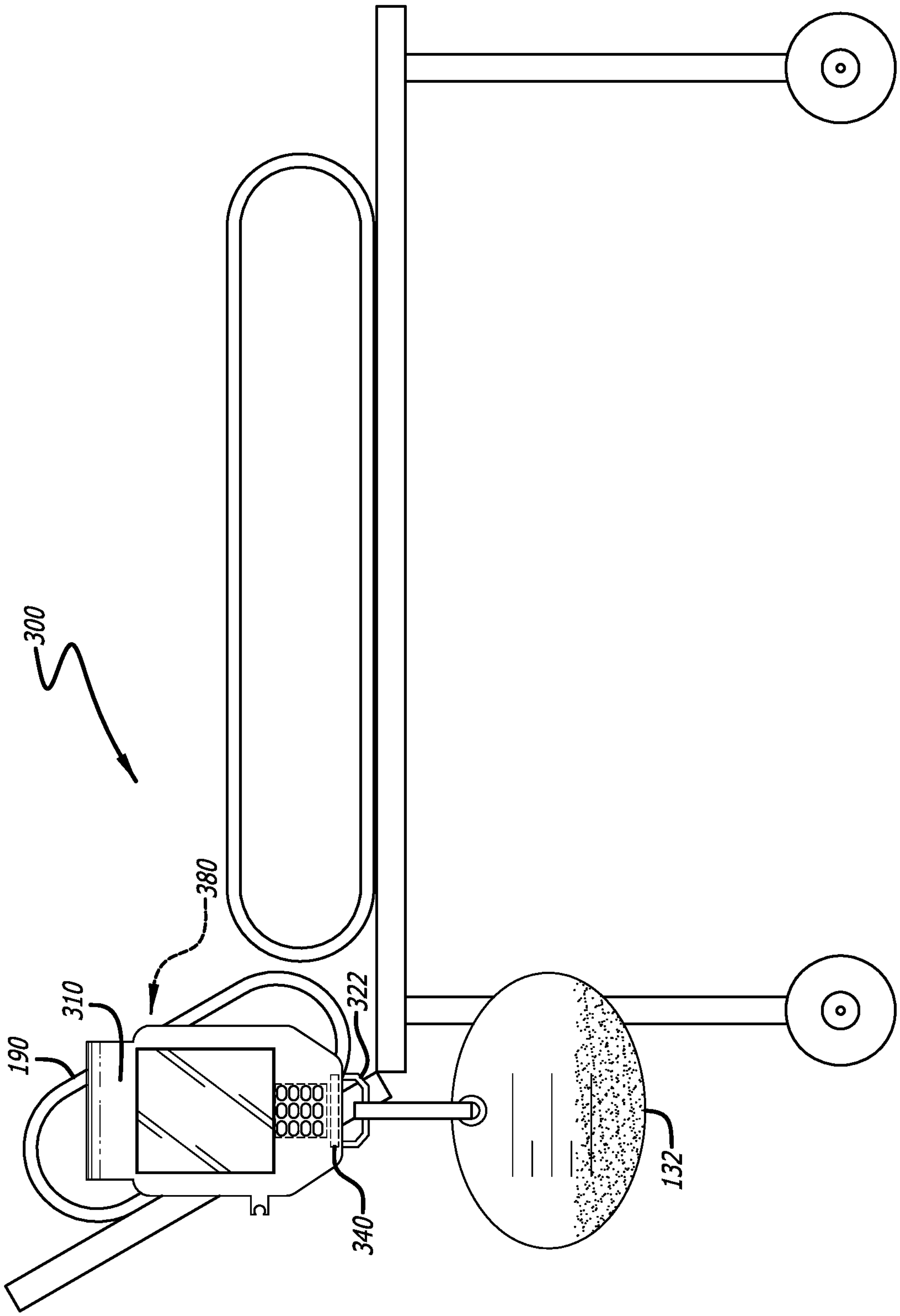

FIGS. 5A-5B illustrate a perspective view of the system 300 depicting an exemplary method of the mounting system 380 maintaining the system 300 in the perpendicular position, in accordance with some embodiments. As illustrated in FIG. 5A, the device 310 may be coupled to the stabilizing surface 190 by the mounting system 380 with the fluid collection bag 132 coupled to the fluid collection bag attachment 322. The stabilizing surface 190 may include a portion of a hospital bed being in a parallel configuration, wherein the parallel configuration includes the portion of the stabilizing surface 190 being parallel to a floor surface. The stabilizing surface 190 may transition from the parallel configuration towards a perpendicular configuration, wherein the perpendicular configuration includes the portion of the stabilizing surface 190 being perpendicular to the flood surface. The mounting system 380 (e.g., the buffering region 384) may allow the device 310 to be rotated around the lateral axis to maintain the device 310 in the perpendicular position, as illustrated in FIG. 5B. The device 310 is continuously coupled to the stabilizing surface 190 while maintaining the perpendicular position. Advantageously, maintaining the device 310 and more specifically the load cell assembly 340 perpendicular to the ground allows the load cell assembly 340 to accurately detect the load of the fluid collection bag 132.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An automated urinary output monitoring system, comprising:

an automated urinary output monitoring device, comprising:

a device body;

a mounting system operatively coupled with the device body, the mounting system including:

a mounting surface rotatably coupled with the device body, the mounting surface configured to secure the automated urinary output monitoring device to an external stabilizing surface; and a buffering region disposed between the mounting surface and the device body, the buffering region configured to transition between a non-compressed configuration and a compressed configuration along a lateral axis to isolate the device body from vibrations of the external stabilizing surface or lateral movement of the external stabilizing surface;

a load cell assembly operatively coupled with the device body; and a fluid collection bag attachment coupled with the load cell assembly, the fluid collection bag attachment configured to suspend a fluid collection bag therefrom; and a console communicatively coupled with the load cell assembly, the console including one or more processors, and non-transitory computer readable medium having logic stored thereon that, when executed by the one or more processors, performs operations, including:

receiving a load value applied to the fluid collection bag attachment by the fluid collection bag; and calculating a volume of urine collected within the fluid collection bag based on the load value; and depicting the volume of urine on a display of the automated urinary output monitoring system.

2. The system according to claim 1, wherein the automated urinary output monitoring device includes a tube holder coupled with the device body, the tube holder configured to secure a portion of a drainage tube of the fluid collection bag to the device body.

3. The system according to claim 1, wherein the mounting system extends laterally away from a back panel of the device body.

4. The system according to claim 1, wherein the mounting surface includes a mounting mechanism including a number of suction cups, clamps, magnets, or an adhesive configured for securing the mounting surface to the external stabilizing surface.

5. The system according to claim 1, wherein the mounting surface is configured to rotate with respect to the device body to maintain a vertical orientation of the device body during use.

6. The system according to claim 1, wherein the automated urinary output monitoring device is configured to rotate with respect to the mounting surface due to gravity when the mounting surface is secured to the external stabilizing surface.

7. The system according to claim 1, wherein the mounting surface rotates about an axis of rotation extending through the buffering region.

8. The system according to claim 1, wherein the automated urinary output monitoring device includes a securing attachment extending upward away from a top side of the device body, the securing attachment configured to suspend the automated urinary output monitoring device from a bed rail.

9. The system according to claim 1, wherein the automated urinary output monitoring device includes a front panel including the display and an input interface, each in communication with the console.

10. The system according to claim 9, wherein the input interface includes a plurality of buttons.

11. The system according to claim 1, wherein the automated urinary output monitoring system receives electrical power from an external power source.

12. The system according to claim 1, wherein the operations further include:

correlating the volume of urine with a time of day; and depicting the time of day along with the volume of urine on the display.

13. The system according to claim 2, wherein the automated urinary output monitoring device includes one or more module inputs configured to define communication between one or more modules and the console.

14. The system according to claim 13, wherein:

the one or more modules includes a temperature sensor coupled with the tube holder, the temperature sensor configured to measure a temperature of urine disposed within the drainage tube; and the operations further include:

obtaining a temperature measurement of the urine disposed with in the drainage tube; and depicting the temperature measurement on the display.

15. The system according to claim 1, wherein:

the console is configured to wirelessly communicate with an external computing device, the external computing device including one or more of a tablet, a cell phone, or an electronic medical record (EMR) system; and the operations further include at least one of:

receiving patient information from the external computing device; or transmitting urine output monitoring data to the external computing device.

16. The system according to claim 15, wherein the operations further include:

receiving a plurality of patient profiles from the EMR system; and storing the plurality of patient profiles on the non-transitory computer readable medium.

* * * * *